United States Patent [19]

Ries et al.

[11] Patent Number: 4,623,553
[45] Date of Patent: Nov. 18, 1986

[54] METHOD OF PRODUCING A BONE SUBSTITUTE MATERIAL

[75] Inventors: Peter Ries, Reinach; Frank Baümgart, Grenchen, both of Switzerland; Heinz Mittelmeier, Homburg-Schwarzenbach, Fed. Rep. of Germany

[73] Assignee: Oscobal AG, Switzerland

[21] Appl. No.: 741,170

[22] Filed: Jun. 4, 1985

[30] Foreign Application Priority Data

Jun. 12, 1984 [EP] European Pat. Off. ......... 84810288.5

[51] Int. Cl.$^4$ .......................... A01N 1/02; A61F 1/00; A61F 1/24; A61F 5/04
[52] U.S. Cl. .................. 427/2; 128/92 YQ; 623/16; 623/18; 623/66
[58] Field of Search .............. 623/16, 18, 66; 128/92 C, 92 G; 427/2

[56] References Cited

U.S. PATENT DOCUMENTS 4,516,276  5/1985  Mittelmeier et al. ............ 128/92 G

*Primary Examiner*—Michael R. Lusignan
*Attorney, Agent, or Firm*—Pravel, Gambrell, Hewitt & Kimball

[57] ABSTRACT

For producing the bone substitute material from collagen and hydroxyapatite, an aqueous solution of cleaned collagen is mixed with a cross-linking agent causing only a partial cross-linking, and the mixture is lyophilized.

The quantity of the cross-linking agent is chosen such that the collagen retains its resorbability and its absorptivity vis-a-vis bodily fluids, the material further showing no undesirable side effects.

Preferably less than 1% by weight of formaldehyde, one of the preferred cross-linking agents, is added, with reference to the dry weight of collagen, and sintered apatite grains with a diameter of 50–300 $\mu$m are used.

Such a bone substitute material is stronger and less tearable as previously known materials and insures a good promotion of the growth of own bone tissue and the substitution by it.

13 Claims, No Drawings

METHOD OF PRODUCING A BONE SUBSTITUTE MATERIAL

BACKGROUND OF THE INVENTION

The patent application refers to a method of producing a partially cross-linked bone substitute material, mainly of collagen and a mineral component consisting of apatite, tricalcium phosphate ($\alpha$ and $\beta$) and/or hydroxyl apatite and/or calcium phosphate ceramics. A method of producing a bone substitute is described in U.S. Pat. No. 4,516,276 of the same assignee. Extensive clinical studies have been published in the German publication "Zeitschrift fur Orthopadie"121 (1983), pages 115-123, H. Mittelmeier, B.D. Katthagen, from where it follows that an encouraging and satisfying success has been obtained.

These studies further showed that the material, in spite of a further termal treatment and chloric acid vaporization, was still relatively delispescent during clinical insertion into the tissue, in particular while soaking the blood and tissue fluids, and that the generation of bone tissue was not marked enough. Accordingly, a more compact material would be desirable, which further would create a better stimulation of the bone growth.

PCT publication No. W 081/00963 discloses a method of producing a collagen material which, after admixing with finely grained apatite, served as bone substitute material for the above-mentioned studies. As mentioned in said publication, an essential increase in the absorbency and the mechanical strength relative to previously known collagen fleeces has been obtained by subjecting the collagen material to a further heat treatment or a treatment with gaseous halide acids.

From the same publication follows that it was known to improve the physico-chemical properties of collagen and gelatine products on a chemical basis, for example by cross-linking with aldehydes, in particular formaldehyde or glutaraldehyde. It is stated that those methods have the drawback that the thus obtained products are resorbed only very slowly or not at all by the body when implantated and cause inflammations, defense reactions or the production of foreign substance macro cells. The cross-linking of the collagen products with aldehydes has been effected in an exhaustive manner, resulting in completely cross-linked, plastic material like products which are recognized by the organism as foreign substance and thus cause the mentioned harmful reactions. Residual quantities of free aldehyde in the implant are also harmful to the tissue.

The publication Jap. Traumat. Surg. (1982) 99, pages 265-269 of K. Hayashi et al discloses a collagen-hydroxyl apatite preparation, which was freeze-dried after cross-linking. On one hand, relatively finely grained apatite has been used and on the other hand no hint has been given that the quantity of the admixed glutaraldehyde should be such that none of the above-mentioned reactions occurs.

SUMMARY OF THE INVENTION

Accordingly, it is an object of the present invention to provide a method for the production of a bone substitute material, which material is more compact and stronger and more tear resistant than previously known material, and which further stimulates the natural bone development to grow at and into the material, without causing the aforementioned undesirable effects.

According to the invention it has been found that a partial cross-linking with formaldehyde or glutaraldehyde instead of a total, exhaustive cross-linking provides for a substantial improvement of the physicochemical properties of the collagen without causing any negative effects to the organism after the implantation or any harm due to remaining quantities of aldehyde.

As mentioned above, finely grained apatite, for example tricalcium phosphate powder with particle sizes of 3-5 $\mu$m has been used for performing the experiments with the known material. It has been found that the osteogenetic efficiency can be increased substantially if the apatite is used in form of powder aggregates or as particles of a larger size. This increase of the particle size can be attained by sintering commercially available fine crystalline apatite or tricalcium phosphate to grains of a diameter of 20-1000 $\mu$m, preferably 50-300 $\mu$m.

Experiments to this effect have shown that bone substitute material consisting of collagen partially cross-linked with formaldehyde and apatite, for example, tricalcium phosphate in the form of sintered grains which are added to the collagen solution before freeze drying furnish substantially improved results over the previously known bone substitute material. This new partially cross-linked material is suited for a wider range of use. It is particularly advantageous to distribute the apatite grains in the collagen analogous to the orientation of cross points of the mineral structures in natural bone, thus providing a matrix for the restitution of the bone which is similar to natural bone.

DESCRIPTION OF THE PREFERRED EMBODIMENTS

The starting material needed for carrying out the method of the invention can be obtained according to the following process:

1 kg bovine tendons were freezed by $-10°$ to $-20°$ C. and reduced to very small pieces during 20 min. with a high speed knife. The temperature of the ground stock was held below $+40°$ C. by adding ice bits. The thus obtained tenacious fibrous tissue pulp was suspended in 5 liters of a 10% NaCl-solution, which contained 2.5 g sodium azide and 50 ml of a 10% aqueous solution of the non-lution of the non-ionic wetting agent NP 55/52 (polyoxyethylen nonoylphenyl ether) under vigorous agitation. The suspension was agitated for two hours at room temperature, than centrifuged. The gray to brownish colored supernatant solution, containing grease and undesired water soluble ballast substances, was rejected. The remaining white skin fibers pulp was twice extracted in the same manner, whereby 0.1 mol disodium hydrogen phosphate was added per liter extraction solution.

It is also possible to use hog skin instead of bovine tendons.

A degreased and extracted fibrous tissue pulp, obtained from 1 kg bovine tendons as described above was suspended in a 5-fold volume of 0.5 M acetic acid. To the suspension was added a solution of 1 g technical pepsin in 100 ml 0.01 N HCl. The pH of the suspension was adjusted with HCl to 2.9. The suspension was digested under continuous agitation for 48 hours. The viscous collagen solution was filtrated through a suction filter to eliminate non-digested particles. The collagen was precipitated by addition of 30% aqueous sodium hydroxide solution from the suspension and separated by centrifuging. The collagen was purified by dissolving in 0.5 M acetic acid and precipitating by slow addition of 3% sodium chloride. The purified collagen was dissolved in 0.5 M acetic acid and diluted with water. The sodium chloride remaining in the collagen was removed by washing on an ultra filter. The ultra filtration was continued until no chloride ions could be detected in the filtrate by addition of nitrate of silver, and the collagen concentration attained about 1%. The collagen solution was filtrated and 0.2% by weight formaldehyde and 5 parts by weight of sintered apatite grains with a diameter of 20–1000 μm, both with reference to the collagen content, were added to the collagen solution, agitated for about 20 min, molded into appropriate forms, rested several hours, lyophilized and sterilized by γ-radiation.

EXAMPLE 1

600 g of ultra-filtrated collagen solution obtained according to the above described process with a collagen content of 0.88% by weight were filtrated clear and mixed with 10.6 ml of a 0.1% aqueous formaldehyde solution and agitated. To the solution was added under agitation 26.4 g sintered apatite grains with a diameter of 50–150 μm and stirred during 22 minutes. The pH of the solution rose during agitated from initial 3.5 to 6.35. The thus obtained, solution was poured into portions of 70 g into polystyrene cups with the dimensions of 12×7.5 cm, kept standing over night, lyophilized the day after, then packed and sterilized by γ-radiation at a dosage of 2.5 Mrad.

EXAMPLE 2

To 800 g of ultra-filtrated collagen solution obtained according to the above-described process with a collagen content of 1.07% by weight was added 6.83 ml of a 25% by weight, aqueous glutaraldehyde solution and 17.2 g, twice the quantity with reference of the collgen content, of sintered apatite, tricalcium phosphate grains with a diameter of 300–700 μm. The mixture was agitated for half an hour, kept standing for 10 hours and poured into portions of 18 g into cups with the dimensions of 6.3×3.8 cm, lyophilized, packed and sterilized by γ-radiation at a dosage of 2.5 Mrad.

EXAMPLE 3

200 g of ultra-filtrated collagen solution obtained according to the above-described process with a collagen content of 0.97% by weight were mixed with 5.82 g, the three times the quantity with reference to the collagen content, of sintered apatite grains of a diameter of about 100 μm. The mixture was agitated for half an hour, poured into portions of 40 g into circular cups with a diameter of 8 cm and lyophilized. The thus obtained material was unstable vis-a-vis aqueous solutions and was therefore partially cross-linked by exposing it to formaldehyde gases for two hours by a closed chamber charged with a 35% in weight formaldehyde solution. Afterwards, the formaldehyde solution was removed and the chamber was evacuated and ventilated 6 times to remove the unbound formaldehyde gas from the collagen apatite material. At the third aeration the air was conducted through an aqueous ammonium hydroxide solution to bond the remaining quantities of the formaldehyde to the incoming ammonia. The thus obtained bone substitute material was stable vis-a-vis aqueous solutions after this treatment and suited for the implantation after sterilization.

It follows from this example that good results can be obtained with a quantity of formaldehyde, which lies under 1% by weight, with reference to the dry weight of the collagen, preferably about 0.05–0.5% by weight. For the use of other aldehydes, a corresponding quantity has to be employed.

Besides the mentioned formaldehyde and glutaraldehydes a saturated or unsaturated, mono- or polyfunctional aliphatic aldehyde, glyoxal, unsubstituted or substituted di- or tri- chlorotriazine can be used. As gaseous cross-linking agent ethylene oxide can be used also.

It is preferable to increase the mechanical strength of the bone substitute material by combining it with a honeycomb layer or textile material (woven, twisted, knitted), supporting elements of plastic, textile, metal, alumina, ceramics, carbon fibers, bone cement, glass fibers or bioglass fibers. Said supporting elements can have the form of the bone to be replaced. It is also possible to add antibiotics to the bone substitute material.

For compacting, the bone substitute material can be compressed in the dry or wet state, if needed under heating.

The foregoing disclosure and description of the invention are illustrative and explanatory thereof and various changes in the size, shape and materials as well as in the details of the preferred embodiment may be made within departing from the spirit of the invention.

We claim:

1. A method of producing a bone substitute material from collagen and a mineral component, said mineral component comprising apatite and/or hydroxyapatite and/or calcium phosphate ceramics, wherein an aqueous solution or a dispersion of cleaned collagen is mixed with a cross-linking agent of a quantity so as to result only in a partial cross-linking, whereby the quantity of said cross-linking agent is chosen such that the collagen is cross-linked only to such a degree that it retains its resorbability and its adsorptivity vis-a-vis bodily fluids and that the material does not generate undesirable side effects, and the mixture is lyophilized.

2. A method according to claim 1, wherein said mineral component is apatite, in particular sintered hydroxyl apatite or calcium phosphate with a grain diameter of 20–1,000 μm, preferably 50–300 μm.

3. A method according to claim 1, wherein the proportion of collagen to the mineral component is from 1:2 to 1:10, preferably from 1:3 to 1:5.

4. A method according to claim 1, wherein an aqueous solution or dispersion of cleaned collagen is mixed with the mineral component grains, the mixture is lyophilized and the thus obtained lyophilisate is treated with a gaseous cross-linking agent.

5. A method according to claim 4, wherein the gaseous cross-linking agent is gaseous formaldehyde or ethylenoxide.

6. A method according to claim 1, wherein the cross-linking agent is a saturated or unsaturated, mono- or poly-functional aliphatic aldehyde.

7. A method according to claim 6, wherein said aldehyde is formaldehyde, glutaraldehyde or glyoxal.

8. A method according to claim 1, wherein the partial cross-linking of the collagen is effectuated with formaldehyde in a quantity below 1% by weight, preferably 0.05–0.5% by weight, with reference to the dry weight of the collgen, or the equivalent quantity of another aldehyde.

9. A method according to claim 1, wherein the cross-linking agent is an unsubstituted or substituted di- or trichlorotriazine.

10. A method according to claim 1, wherein an antibiotic is added to the collagen and mineral component or to the material produced from it.

11. A method according to claim 1, wherein said bone substitute material is piled up on a honeycomb-like or porous basic structure.

12. A method according to claim 11, wherein the honeycomb-like basic structure is made of plastics material, textile, metal, ceramics, carbon fibers tissue or bone cement.

13. A method according to claim 1, wherein the bone substitute material is compressed in a dry or wet state, with or without heat treatment.

* * * * *